United States Patent [19]

Barrett

[11] Patent Number: 4,469,103

[45] Date of Patent: Sep. 4, 1984

[54] METHOD OF TREATING CONDITIONS SUCH AS TUMORS IN LIVING BODIES

[76] Inventor: Harold F. Barrett, Rte. 1, Box 262A, London, Ark. 72847

[21] Appl. No.: 354,361

[22] Filed: Mar. 3, 1982

[51] Int. Cl.³ ............................................. A61F 7/00
[52] U.S. Cl. ..................................... 128/400; 128/401
[58] Field of Search ............... 128/399, 400, 401, 402, 128/396, 804

[56] References Cited

U.S. PATENT DOCUMENTS

| | | | |
|---|---|---|---|
| 1,327,207 | 1/1920 | Lidberg . | |
| 1,572,300 | 2/1926 | Max . | |
| 1,995,302 | 3/1935 | Goldstein | 128/254 |
| 2,058,780 | 10/1936 | Elliott | 128/401 |
| 2,190,384 | 2/1940 | Newman | 128/400 |
| 2,346,245 | 4/1944 | Zichlin | 128/401 |
| 2,466,042 | 4/1949 | Reich et al. | 128/401 |
| 2,734,508 | 2/1956 | Kozinski | 128/401 |
| 3,089,033 | 5/1963 | Fujisawa | 128/399 X |
| 3,496,942 | 2/1970 | Shipley | 128/401 |
| 3,848,607 | 11/1974 | St. Clair | 128/400 |
| 4,121,592 | 10/1978 | Whalley | 128/413 |
| 4,160,455 | 7/1979 | Law | 128/400 |
| 4,181,132 | 1/1980 | Parks | 128/399 |
| 4,190,053 | 2/1980 | Sterzer | 128/399 |

FOREIGN PATENT DOCUMENTS 2731744  2/1979  Fed. Rep. of Germany ...... 128/804

OTHER PUBLICATIONS

Warren, "Preliminary Study . . . Tumor Cases", Am. J. Roent. & Rad. Therapy, vol. 23, No. 1, Jan. 1935, pp. 75–87.
Law et al., "New Apparatus . . . Neoplasia, IEEE Trans. Biomed. Eng., vol. 26, No. 3, Mar. 1979, pp. 175–177.

Primary Examiner—Lee S. Cohen
Attorney, Agent, or Firm—Kerkam, Stowell, Kondracki & Clarke

[57] ABSTRACT

Conditions, such as tumors, in a living body are treated by applying localized infrared electromagnetic energy to the affected area of the body. The energy is selected to have a wavelength such that the energy is absorbed by the cells, and the amplitude of the energy is adjusted to a value that is effective to cause destruction of defective cells without destroying healthy cells. Preferably, the energy is derived from a flowing fluid having a temperature within the normal operating temperature range of the body, which determines the wavelength of the energy, and the amplitude of the energy is adjusted by controlling the flow rate of the fluid.

20 Claims, 3 Drawing Figures

METHOD OF TREATING CONDITIONS SUCH AS TUMORS IN LIVING BODIES

BACKGROUND OF THE INVENTION

This invention relates generally to the treatment of living beings, and more particularly to the treatment of conditions such as tumors in humans and other animals.

Conditions such as tumors in living bodies are treated non-surgically by a variety of different methods, including chemotherapy, radiation therapy, hyperthermia, and combinations thereof. These methods have as their objective the selective destruction of tumor cells. Hyperthermia, for example, which involves the application of heat to an affected area of the body, is based upon the principle that certain tumor cells have a lower temperature tolerance than normal healthy cells. Consequently, such tumor cells can be destroyed by elevating their temperature to a predetermined level above the normal body temperature. It is known that the cells of certain types of tumors can be destroyed by heating them to temperatures of the order of 110° F. Hyperthermic treatment of tumors may be accomplished by perfusion techniques, as by irrigating a body cavity adjacent to the tumor with hot water ducted into and out of the cavity by pipes, or by localizing and heating the blood flowing through a limb containing the tumor. Diathermy and other radio frequency electric fields may also be employed to produce heating.

Such treatment methods have a number of disadvantages. They may not be effective against certain types of tumors, or against tumors located in certain portions of the body. Certain treatment methods, such as chemotherapy and radiation therapy, have well-publicized undesirable side effects, and with all known treatment methods it is difficult to avoid damage or destruction of healthy cells in the surrounding tissue.

There is a need for more effective methods of treating conditions such as tumors in living bodies, and that avoid the disadvantages of known methods, and it is to this end that the present invention is principally directed.

SUMMARY OF THE INVENTION

The invention provides new and improved methods of treating conditions such as tumors in living bodies that do not rely upon conventional radiation therapy, chemotherapy, or hyperthermic techniques. The invention enables the selective destruction of defective cells with little or no damage to healthy cells and few if any adverse side effects. Treatment methods in accordance with the invention have been shown to be remarkably effective in destroying tumors in very short periods of time, and may be practiced with simple apparatus.

Briefly stated, the invention involves applying localized infrared electromagnetic energy of selected wavelengths to an affected area of the body, and adjusting the amplitude of the energy to a value that is effective to cause substantial destruction of defective cells without substantially destroying healthy cells. In a preferred form, the infrared electromagnetic energy is derived from a flowing fluid having a temperature within the normal operating temperature range of the body, and a flow rate that is adjusted to provide the desired energy amplitude.

More particularly, the infrared electromagnetic energy is selected to have a dominant wavelength, in the 9–10 micron range, for example, that is matched to the cell sizes of the living body so that the cells absorb the energy efficiently. The wavelength distribution of the energy is related (by Wien's Law) to the absolute temperature of the flowing fluid, which is preferably selected to be within the normal operating temperature range of the living body. The amplitude of the energy is related to the flow rate of the fluid, and, in general, is proportional thereto.

DETAILED DESCRIPTION

Figure 1:
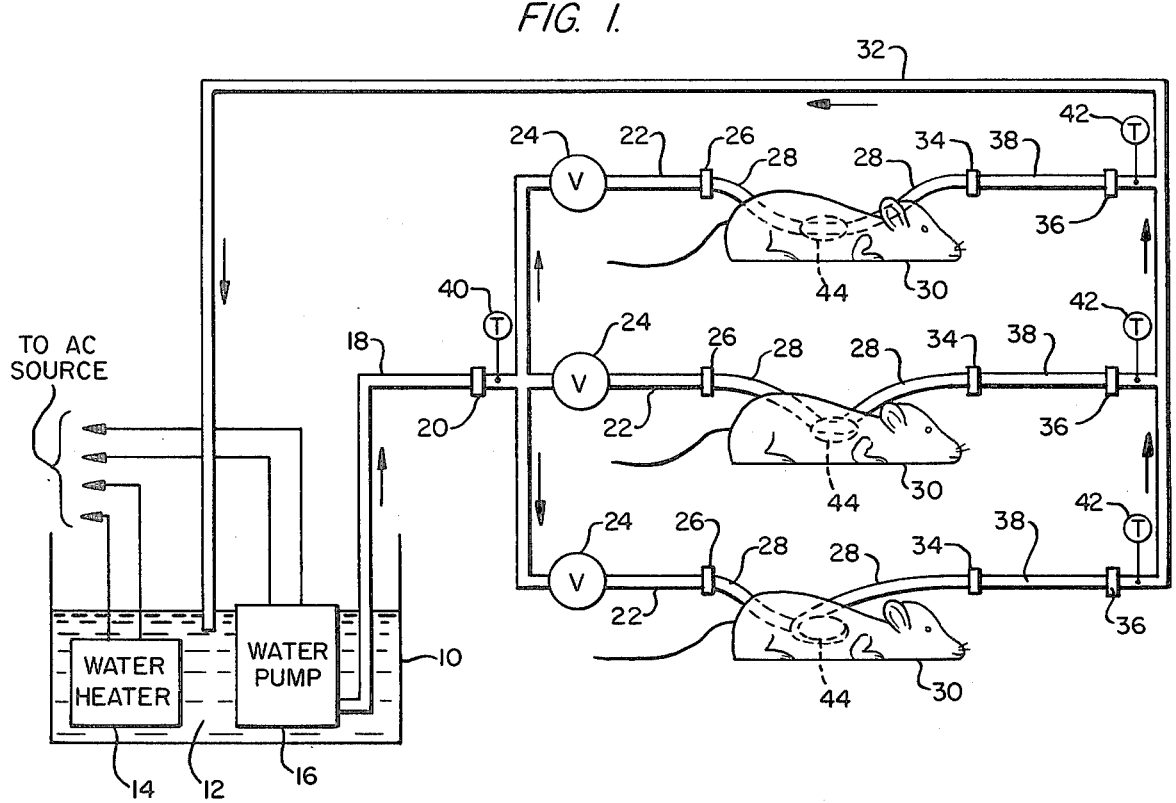
FIGS. 1 and 2 are diagrammatic views that illustrate, respectively, heated water systems that may be employed for practicing the invention.
Figure 2:
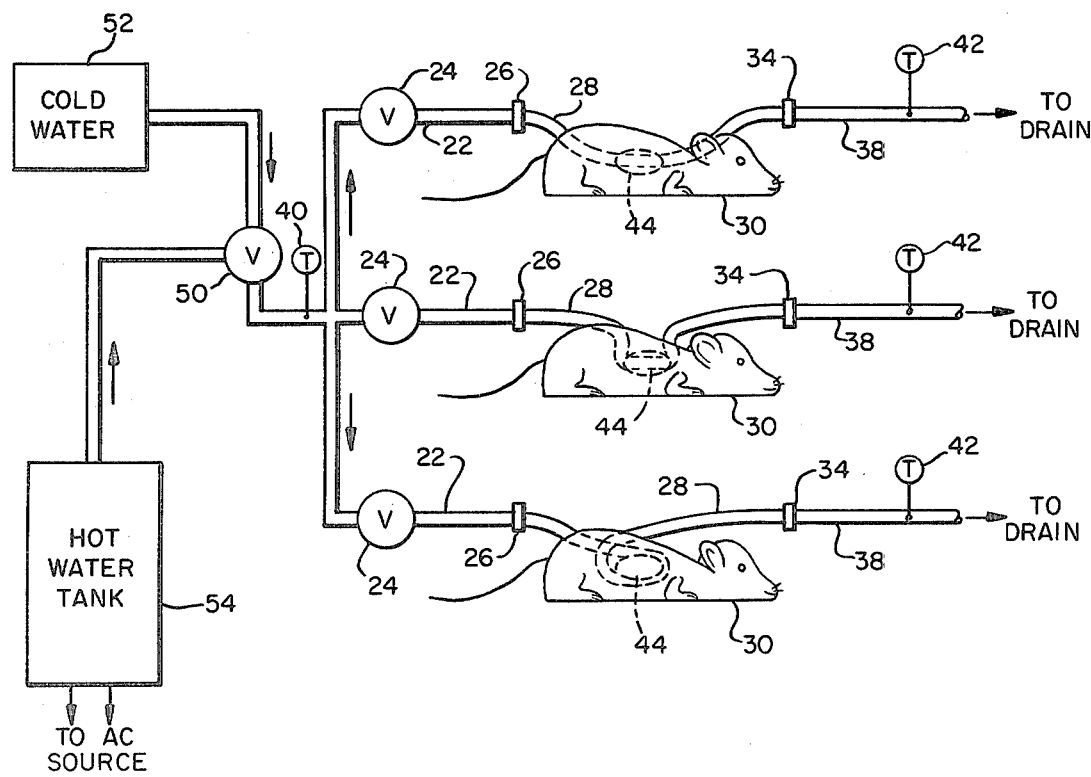
Figure 3:
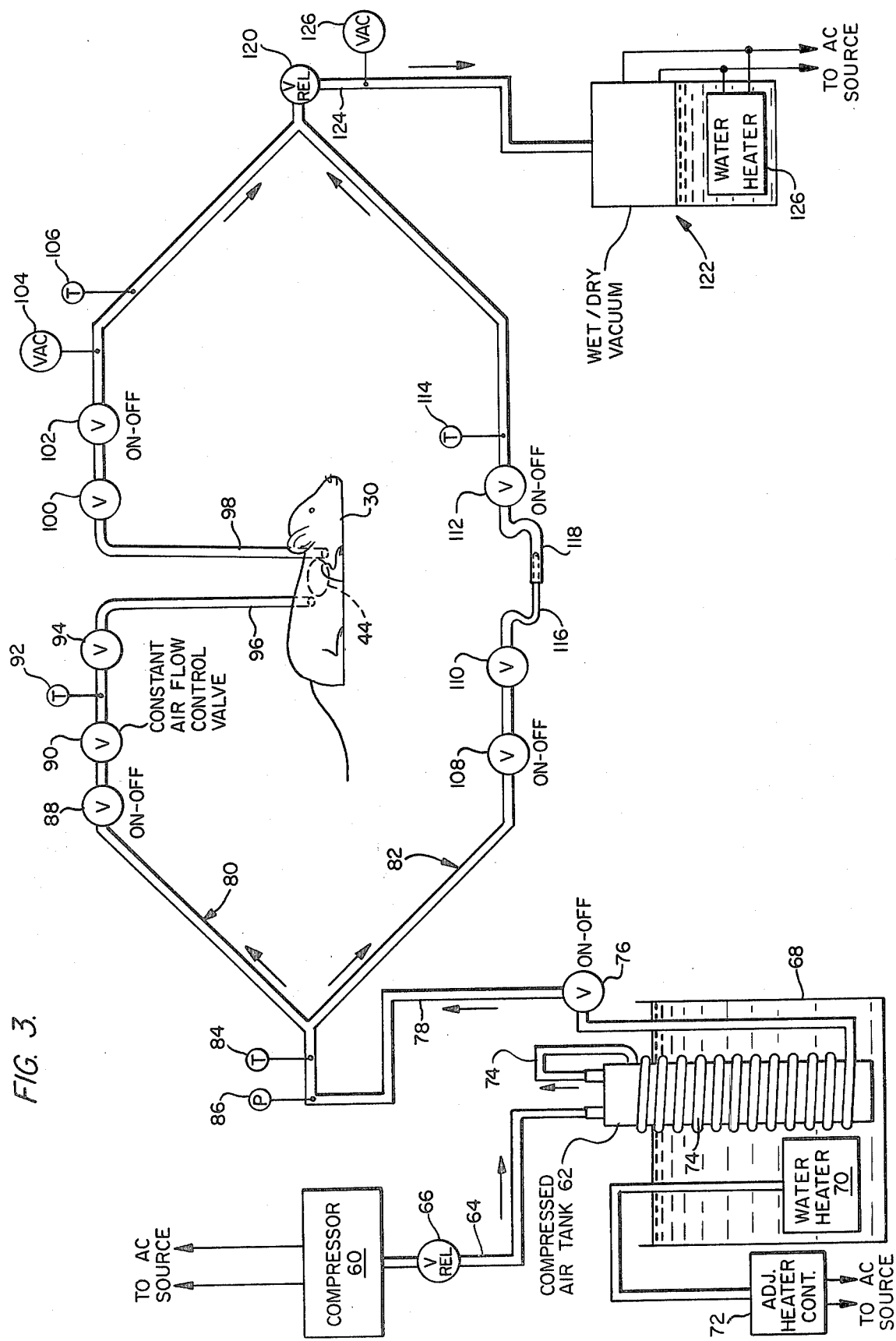
FIG. 3 is a diagrammatic view that illustrates a heated air system which may be employed for practicing the invention.

As indicated above, the invention involves the application of infrared electromagnetic energy to living bodies to treat conditions such as tumors. Although the infrared electromagnetic energy may be derived from different sources, a particularly simple and effective source of such energy is a flowing fluid, and FIGS. 1–3 illustrate fluid systems of the type which may be employed for practicing the invention. The systems illustrated in these figures were actually constructed and employed in a series of experiments on laboratory mice infected with a certain type of tumor in order to prove the invention. The systems are not necessarily optimized, but are merely representative of systems that may be employed for practicing the invention. It will be appreciated by those skilled in the art that a number of improvements can be made in these systems, and that different types of systems may be employed for practicing the invention. Moreover, for treating animals other than mice, it will be appreciated that certain other changes may be desirable.

Prior to discussing the treatments that were conducted on the laboratory mice (which are described in detail in the Examples given hereinafter), the systems of FIGS. 1, 2 and 3 will be briefly described. Next, the Examples describing the results of the experiments conducted on the laboratory mice will be discussed, and, following the Examples, a theoretical explanation for the remarkable results achieved by the invention will be presented.

FIG. 1 illustrates a heated water system that may be employed for practicing the invention. As shown, the system may comprise a water container 10 for storing a quantity of water 12 (3 gal., for example). A submersible electric water heater 14 and an electric water pump 16 may be located within the container to enable heated water to be pumped to a water supply line 18, which may be standard ⅜ in. diameter plastic tubing. From an interface connector 20, the water supply line may branch to a plurality of lines 22 (three such lines being illustrated in the figure), each line having an adjustable flow valve 24 therein to enable adjustment of the water flow rate through the line. Each line 22 may be connected, by means of a connector 26, to one end of a length of tubing 28 that is partially implanted within the body of a laboratory test mouse 30. The other end of each length of tubing 28 may be connected to a common return line 32, that empties into container 10, by means of connectors 34 and 36 and lines 38, as shown. An in-line temperature gauge 40, which may be a thermometer, adjacent to interface connector 20 enables the temperature of the water entering lines 22 to be monitored, and another in-line temperature gauge 42 adjacent to each connector 36 enables the temperature of the water flowing through each branch of the system into the return line to be monitored.

Tubing 28 may be a type TW-19 medical infusion set comprising plastic tubing having an inner diameter of approximately 0.047 in. and a wall thickness of approximately 0.010 in. The plastic tubing is somewhat transparent to infrared electromagnetic energy in the range of interest, and a portion of the tubing may be surgically implanted within the body of the test mouse adjacent to an affected area 44, e.g., a tumor, preferably in contact with and partially surrounding the affected area. Valves 24 enable independent adjustment of the water flow rate through the tubing 28 implanted in each mouse, and conventional means (not illustrated) may be employed for measuring the flow rate. The temperature applied to the affected area of each mouse is, to a close approximation, the average of the temperature reading of gauge 40 and the temperature reading of the gauge 42 monitoring the water temperature flowing from the mouse into the return line. Water heater 14 may be controlled in a conventional manner to provide the desired temperature.

FIG. 2 illustrates another form of a heated water system that may be employed for practicing the invention. The system of FIG. 2 is somewhat similar to the system of FIG. 1 except that it is not a closed loop system. (The same reference numerals are used to designate parts of each system which may be the same.) As shown, instead of employing a submersible water heater and water pump for supplying heated water, a mixing valve 50, which may be a conventional mixing faucet supplied with cold water 52 and hot water from a conventional hot water tank 54, may be employed as a source for heated water. The temperature of the water supplied to each branch of the system may be regulated by adjusting mixing valve 50 while monitoring the temperature using temperature gauge 40. Also, the water flowing through each branch of the system may be simply drained away, thereby eliminating the need for a return line. As with the system of FIG. 1, the flow rate through each branch of the system of FIG. 2 may be independently adjusted by valves 24.

Although the heated water systems of FIGS. 1 and 2 have the advantage of being rather simple, the heated air system of FIG. 3 is preferred. As shown, the heated air system may comprise a compressor 60 that supplies compressed air to a compressed air storage tank 62 by means of a line 64 containing a pressure relief valve 66. The compressed air tank may be located in a tank of water 68 containing a submersible water heater 70 controlled by an adjustable heater control 72 for heating the water in the tank. The outlet line 74 from the compressed air tank, which may comprise 700 feet of ¼ in. diameter plastic tubing, for example, may be wrapped around the outside of the tank to enable the compressed air flowing therethrough to be heated by water. The outlet line is then connected to an on-off adjustable flow control valve 76, the outlet of which may be connected to a supply line 78, as of ½ in. diameter rubber hose, that branches into first and second lines 80 and 82 that form parallel flow paths. An inline temperature gauge 84 and a pressure gauge 86 may be included in supply line 78 for monitoring the temperature and pressure, respectively, of the air flowing into the branching lines.

The upper line (in the figure) 80 may include, in series, an on-off valve 88, a constant air flow control valve 90, an in-line temperature gauge 92 and a vernier flow control valve 94. The outlet of vernier flow control valve 94 may be connected to a length of flexible plastic tubing 96 having one end adapted to be implanted within the body of a mouse 30. Tubing 96 may comprise 5/32 in. I.D., 15/64 in. O.D. flexible plastic tubing, and constitutes an air inlet line, as will be explained shortly. Another length of flexible tubing 98, also adapted to have one end implanted within the body of the mouse, connects to another vernier flow control valve 100 in series with an on-off control valve 102, a vacuum gauge 104 and an in-line temperature gauge 106. Tubing 98 constitutes an air outlet line and may comprise 15/64 in. I.D. flexible plastic tubing.

In the lower flow path 82, an on-off control valve 108, a vernier control valve 110, an on-off control valve 112, and an in-line temperature gauge 114 may be connected together in series, as shown. The vernier control valve 110 and on-off control valve 112 may be connected together by lengths of flexible tubing 116 and 118 of the same size and type as tubing 96 and 98 employed in the upper flow path, by inserting the end of tubing 116 into the end of tubing 118.

The two flow paths may come together at an adjustable vacuum relief valve 120 and are connected to a wet/dry vacuum system 122 via a line 124, as of ½ in. diameter rubber hose. A vacuum gauge 126 may be inserted within line 124 for monitoring the vacuum. As shown in the figure, the wet/dry vacuum system may include a water heater 126. All exposed air pressure lines may be insulated by wrapping them with fiberglass.

Using the system of FIG. 3, an air flow having an adjustable flow rate and temperature may be applied to a tumor 44 or other affected area of the mouse. The compressor portion of the system comprising compressor 60, compressed air tank 62, water heater 70 and their associated components provides a source of heated pressurized air that may be pumped into the mouse via air inlet line 96. The vacuum portion of the system comprising the wet/dry vacuum 122 and its associated control valves enables air to be moved from the mouse's body at the same rate it is being supplied by the compressor portion of the system, thereby providing a balanced air flow through the mouse. The lower flow path 82 of the system serves as a bleed path that facilitates control of the air flow through the upper path.

In operation, assume that it is desired to provide an air flow having a temperature of approximately 102° F. and a flow rate of approximately 2.4 cubic feet per minute (CFM). The dominate wavelength ($\lambda$) of the energy is (by Wien's Law):

$\lambda = 2898/T(°K)$ microns, where T(°K) is the absolute temperature in degrees Kelvin. At 102° F., $\lambda$ is approximately 9.29 microns. To set up the system, water heaters 70 and 126 are turned on and heater control 72 is adjusted until the water in tank 68 is approximately 150° F. Lines 96 and 98 in the upper flow path may be connected together, as by inserting line 96 into 98 (prior to implanting the lines in the mouse), and all on-off control valves and vernier flow control valves are opened. The compressor and vacuum are then started and the system is allowed to stabilize for approximately an hour or until temperature gauge 84 reads approximately 115° F. Vernier flow control valve 110 in the lower flow path may be then adjusted to a convenient mid-point setting, and the pressure adjusted for a pressure reading of approximately 1 psig on pressure gauge 86. Control valves 88 and 102 are then turned off, and lines 96 and 98 are connected to a small rubber balloon. Control valves 88 and 102 are then slowly opened, and the vacuum relief valve 120 is adjusted until the pressure of the air flow in line 96 is equal to the vacuum in line 98. This produces a balanced flow so that the balloon will neither inflate nor deflate.

The temperature at temperature gauge 92 is then adjusted for a reading of approximately 103° F. This may be accomplished by adding or removing fiberglass insulation from the various lines, and by control of the adjustable heater control. At this point, the temperature reading of gauge 84 may be approximately 115° F., and vacuum gauge 104 should read approximately 0. (The vacuum gauge shows a reading only if the vacuum line becomes plugged.) The expected temperature of the air flow in lines 96 and 98 should be approximately 102° F. ±1° F., which can be checked by disconnecting the lines and inserting a thermometer in line 96, and the air flow rate should be approximately 2.4 CFM. If desired, a conventional flow rate measuring device may be included in air flow path 80 to facilitate flow rate adjustments.

The mouse may be connected to the system for treatment, after first being anesthetized, by closing on-off control valves 88 and 102 and vernier flow control valves 94 and 100. Two small incisions may then be made in the mouse's body adjacent to opposite sides of the tumor. Lines 96 and 98 may be inserted into the mouse's body and positioned so as to produce an air flow across the tumor. The lines may be taped down to prevent their movement, and valves 88 and 102 may be opened. Vernier control valves 94 and 100 are then simultaneously and slowly opened so as to maintain a balanced air flow, until they are both fully opened. The mouse is then being treated with external infrared electromagnetic energy derived from the flowing air.

A large number of laboratory mice, most of which were infected with a B-16 solid melanoma (cancerous tumor) were treated with externally applied infrared electromagnetic energy of different wavelengths and amplitudes using the systems of FIGS. 1–3, as will be described shortly in the following Examples. Laboratory mice infected with B-16 melanoma are commonly used in the testing of anti-cancer treatments. The production of such tumors by standard techniques is well known, and the details of these techniques are not germane to the present invention. The normal life-span for untreated infected mice was 21 to 24 days after injection of the B-16 melanoma, as determined from a control group of infected mice that were untreated. It was found, as will be described shortly, that at very low energy amplitudes (corresponding to very low flow rates) tumor cell multiplication was actually enhanced, causing the tumors to increase in size relative to the tumors of the control group. At high energy amplitudes, destruction of both healthy and defective cells was found to occur. However, by adjusting the energy amplitudes to values within an optimum range, it was found that significant and selective destruction of tumor cells could be achieved without adversely affecting good or healthy cells.

The normal operating temperature range of mice is approximately 96° F. to 102° F., which corresponds to an infrared electromagnetic energy wavelength of approximately 9.38 to 9.28 microns, and is approximately the same as the normal operating temperature of humans. In the Examples which follow, the temperature of the flowing fluid which was employed as a source of infrared electromagnetic energy was held approximately constant at 102° F., which was found to be a comfortable temperature for the mice.

EXAMPLE I

A first group of 34 infected mice was treated with externally applied infrared electromagnetic energy derived from flowing water using the system of FIG. 1. Various flow rates in the range of 1 ounce every 15 to 60 seconds, corresponding to very low or low amplitude levels, were employed, and the exposure or treatment time was varied from 2–24 hours. During treatment, the temperature of the flowing water was held approximately constant at 102° F. ±1½° F.

Five mice were treated 8 days after injection of the melanoma using a flow rate of the order of 1 ounce every 60 seconds, which corresponds to a very low energy amplitude. During treatment, the mice ate food and drank water, and showed no signs of pain or discomfort. The life-span (after injection) of these mice was found to be 13–17 days, which represents an average decrease of approximately 33% from the normal life-span of 21–24 days for untreated mice. A correlation was found between treatment time and life-span. Generally, the longer the treatment time, the shorter the life-span. Mice treated for 6–8 hours had a life-span of 13–14 days. Mice treated for 2–4 hours had a longer life-span of 16–17 days. This indicates that at very low amplitudes, tumor cell multiplication rates were increased over and above the multiplication rate without treatment, and very low energy amplitudes actually encourage tumor growth.

Another group of 5 mice was treated 9 days after injection of the melanoma using flow rates of the order of 1 ounce every 15–30 seconds, corresponding to low energy amplitudes. The mice in this group lived 30–40 days after injection of the melanoma, corresponding to an average increase in life-span of approximately 55% over untreated mice. Again, a correlation was found between treatment time and life-span. However, in contrast to the first group of 5 mice, mice treated for the longest periods of time had the longest life-spans. Mice treated for 6–8 hours lived 36–40 days, whereas mice treated for 2–4 hours lived 30–32 days. All mice showed reduction in tumor size, and it was apparent that although the multiplication rate of tumor cells exceeded the destruction rate, the multiplication rate was slowed down relative to untreated mice.

Prior to conducting the above-described treatments on the 2 groups of 5 mice, a group of 24 mice was treated using different flow rates, different temperatures, and different treatment times, and the results of these treatments was used to establish the treatment parameters of the above-described treatments on the 2 groups of 5 mice.

EXAMPLE II

A group of 9 mice infected with B-16 melanoma were treated by applying external infrared electromagnetic energy of medium amplitude levels using the system of FIG. 2. The temperature of the water flow internal to the mice was adjusted to be 102° F. ±1½° F. Twenty-four hours after treatment, the mice were sacrificed and opened up to enable visual inspection of the tumor.

Of the 9 mice, a first group of 3 mice was treated 8–9 days after injection of the B-16 melanoma using a flow rate of approximately 1 ounce every 1.3–1.6 seconds. Treatment time was 2 hours and 15 minutes. These mice showed visual evidence of large-scale tumor cell destruction. The tumor was dark, nearly black in appearance, very dry, and approximately 50% smaller in size than it was prior to treatment. There was no evidence of good cell damage.

The remaining 6 mice were treated for approximately 1½ hours with a flow rate of 1 ounce every 1.5–1.7 seconds. These mice also showed visual evidence of large-scale tumor cell destruction, although to a lesser degree than shown by the first group of 3 mice, indicating a correlation between exposure time and the amount of tumor cell destruction.

It was found that when the surgically implanted tube carring the heated water was next to or very close to the tumor (within approximately ⅛ in.) with the flow rate adjusted to produce tumor cell destruction, the tumor was dark, dry, and smaller in volume after treatment. However, when the tube was greater than approximately ⅛ in. from the tumor, the tumor remained glossy and jelly-like and showed little evidence of tumor cell destruction.

As a result of the above-described treatments (Examples I and II), it is evident that there is a correlation between the amplitude of externally applied infrared electromagnetic energy and the growth rate or destruction rate of tumor cells. At very low energy levels, it appears that the energy is beneficial to the tumor cells and can enhance their rate of multiplication. However, higher energy levels appear to cause tumor cell destruction, and the rate of destruction appears to be related to the amplitude of the energy and to the time for which it is applied.

It is well known, and has been documented, that the maximum blood flow rate in an athlete (who is in good physical condition and after an appropriate warm-up period) during heavy exercise is of the order of 17 ounces per second. Accordingly, it is believed that heated water flow rates of the order of 15 ounces per second would result in an optimum destruction rate of tumor cells without damage to good cells. However, such flow rates are difficult to achieve in the systems of FIGS. 1 and 2 since tubes that are transparent to the infrared electromagnetic energy and that can withstand the high pressures necessary for such flow rates without bursting are difficult to find. These problems are avoided by the heated air system of FIG. 3.

EXAMPLE III

In order to determine the effect on healthy cells of different energy amplitudes, 2 dozen healthy mice with no melanoma were treated with the system of FIG. 3 using heated air as the source of infrared electromagnetic energy. The temperature of the air internal to the mice was held constant at approximately 102° F. ±1° F., and the air flow rate was varied. It was determined that an optimum flow rate (corresponding to an optimum energy amplitude) occurred at approximately 2.4 cubic feet per minute (CFM). At this flow rate, there were no signs of healthy cell damage after 2 or more hours of treatment, and the mice appeared to have greater physical energy than before treatment. At higher flow rates (higher energy amplitudes) damage to good cells resulted, and it was found that a mouse could be killed within a matter of minutes at a flow rate of approximately 2.85 CFM.

Next, tests were conducted on 8 mice that had been injected with B-16 melanoma. Four mice were kept as controls and 4 mice were treated with the system of FIG. 3 using a flow rate slightly less than the optimum flow rate established above. The treatment time was 45 minutes and the temperature of the air applied to the tumor was held at approximately 102° F. ±1° F. Immediately after treatment, the mice were opened up and the treated mice were compared with the control mice. The tumor of all 4 treated mice was dark, nearly black, dry and flattened out. The tumors were at least approximately 20% smaller than the size of the smallest tumor in the control mice. There was no evidence of any good cell damage.

Tests were next conducted on 6 additional mice that had been infected with B-16 melanoma. Three mice were treated and 3 mice were kept as controls. The 3 mice were treated at the same temperature and at the optimum flow rate as above, but the treatment time was extended to 1½ hours. After treatment, the mice were left alive for 18–36 hours. They were then opened up and compared with the control mice.

One of the treated mice was opened up 18 hours after treatment, and the other 2 treated mice were opened up 36 hours after treatment. All 3 treated mice showed visible evidence of tumor destruction, but no evidence of good cell damage. The tumors of the treated mice were nearly black in color, completely dry and flattened out. In contrast, the tumors of the control mice were dark red in color, very wet looking and thick. Laboratory analysis of the tumors of treated mice later confirmed that the tumor nucleus was totally destroyed and there was no new growth. On the average, 5% of the tumor cells were alive after treatment, corresponding to a defective cell destruction of approximately 95%. The laboratory analysis also showed that there was no good cell damage.

Based upon these results, it is estimated that 100% destruction of tumor cells can be obtained by increasing the treatment time, and that no good cell damage will occur as long as the energy amplitude is maintained at or slightly less than optimum. For large tumors, two or more treatments may be necessary for complete destruction. As a guideline, it is estimated that the maximum treatment time in any 24 hour period should not exceed the normal awake time of the animal.

From the foregoing, it may be appreciated that the invention achieves remarkable results and has significant advantages over many prior art treatment methods. There are apparently no undesirable side effects associated with the invention, as there may be with chemotherapy or radiation therapy. In fact, the invention appears to have very beneficial side effects in that the externally applied infrared electromagnetic energy actually appears to beneficially energize healthy cells. Moreover, the invention does not rely upon heating defective cells to an abnormally high temperature in an effort to destroy them, as do some prior art hyperthermic treatment methods. The temperatures employed in the invention are within the normal operating temperature range of the body. Thus, the possibility of destroying healthy cells by excessive heat is avoided.

Although the precise reasons for the remarkable results achieved by the invention are not entirely known, it may be theorized that under normal conditions the cells within a living body absorb infrared electromagnetic energy derived from the blood flowing through the blood vessels. The infrared electromagnetic energy passes through the blood vessel walls to the cells, and is believed to supply the major energy requirements of the cells. The energy has a wavelength distribution and a dominant wavelength that is related to the blood temperature, and the amplitude of the energy supplied to the cells is proportional to the blood flow rate. The infrared electromagnetic energy causes the cells to expand and to resonate at a frequency dependent upon cell dimensions, thus providing a work potential. Good cells have thin outer walls, are highly elastic, and are tightly bound to other good cells. As a result, the infrared electromagnetic energy is distributed or amortized over large numbers of cells. However, as the wavelength of the infrared electromagnetic energy decreases (frequency increases) due to a body temperature rise, or the amplitude of the energy increases due to an increased blood flow rate, greater quantities of energy are supplied to the cells. If the frequency or the amplitude of the energy supplied to the cells becomes too great, the cells may be unable to absorb the energy and may be destroyed by breaking of the cell wall.

Cancer cells (and perhaps most virus-infected cells) are possibly defective body cells that are constantly being produced by various organs and tissues in the body. Under normal conditions, such defective cells are destroyed by the ambient infrared electromagnetic energy inside of the body. Defective cells are generally about the same size and have many of the same characteristics as the good cells of the specific organ or tissue that produces them. Thus, they absorb energy of the same wavelengths as good cells. However, they generally have thicker outer walls than do good cells and are not as elastic. Defective cells are also more loosely bound to each other than are good cells. As a result, defective cells are unable to withstand as high an energy level as good cells, and under normal conditions are constantly being destroyed by the ambient energy within the body.

Under certain circumstances, defective cells may multiply at a faster rate than they are destroyed by the body. Externally applied infrared electromagnetic energy at very low amplitude levels may actually energize defective cells, causing them to multiply more rapidly than they are destroyed by the body defense system. If the rate of multiplication of defective cells is greater than their rate of destruction, cell groupings may grow and a tumor may be formed. Deleterious external infrared electromagnetic energy at amplitude levels sufficient to cause multiplication of defective cells may enter the body through various means. For example, the ambient air may provide low amplitude infrared electromagnetic energy having frequency and wavelength components that are conducive to defective cell growth. Other sources of low amplitude infrared electromagnetic energy may also encourage tumor growth. Infrared electromagnetic energy which may stimulate defective cell multiplication may also be produced indirectly by X-rays as from medical or dental X-ray equipment, for example. Certain substances, e.g., air pollution or tobacco smoke in the air, may possibly shield defective cell groupings from the ambient infrared electromagnetic energy in the body, allowing the defective cells to multiply.

In accordance with the invention, external infrared electromagnetic energy is applied to an affected area of a living body. Preferably, the energy is derived from a flowing fluid having a temperature within the normal operating range of the body, and has an energy amplitude (related to the flow rate of the fluid) high enough to cause selective destruction of defective cells without causing damage to healthy cells. It is believed that the wavelengths of the infrared electromagnetic energy employed by the invention match the dimensions of cells being treated and thereby enhance the resonant absorption of the energy by the cells. The defective cells, which do not have the same elasticity or the tight inter-cell bonds as good cells, are unable to absorb all of the externally applied energy, and are thus destroyed.

Human beings have a normal body operating temperature range that is approximately the same as mice, i.e., 96° F. to 102° F., which corresponds to energy wavelengths of the order of 9.38–9.28 microns. Based upon the results of the above-described tests on laboratory mice, it is expected that conditions in humans caused by defective cells, such as tumors, can be treated by subjecting the defective cells to external infrared electromagnetic radiation derived from a fluid having a temperature within the normal body operating temperature range, and having an amplitude selected such that the defective cells are destroyed without destroying healthy cells. The optimum amplitude of the energy, which is proportional to the flow rate of fluid, may be determined by varying the flow rate until a value is found at which defective cell destruction is optimized without destroying healthy cells. It may also be appreciated from the foregoing, that other sources of external infrared electromagnetic energy may also be employed for practicing the invention.

While preferred embodiments of the invention have been shown and described, it will be apparent to those skilled in the art that changes can be made in these embodiments without departing from the principles and spirit of the invention, the scope of which is defined in the appended claims.

I claim:

1. A method of treating a condition in a living body that is produced by defective cells comprising applying to an area of the body containing the defective cells localized infrared electromagnetic energy having a wavelength such that the energy is absorbed by the defective cells, the energy being derived from a flowing fluid having a temperature within the normal operating temperature range of the body and the wavelength of the energy being determined by said temperature, and adjusting the amplitude of the energy, by adjusting the flow rate of the fluid, to a value that is effective to substantially destroy defective cells without substantially destroying healthy cells.

2. The method of claim 1, wherein the energy is selected to have a wavelength at which the cells resonate.

3. The method of claim 2, wherein the wavelength is in the 9 to 10 micron range.

4. The method of claim 1 wherein the temperature of the fluid is in the range of about 96° F. to 102° F.

5. The method of claim 1, wherein said condition is a tumor.

6. The method of claim 5, wherein said flowing fluid comprises a gas that is injected into the body adjacent to the tumor and removed from the body such that a gas flow is produced across the tumor.

7. The method of claim 6, wherein the gas that is injected into the body is supplied from a source of pressurized gas that is heated to provide a predetermined gas temperature.

8. The method of claim 7, wherein the gas is injected into and removed from the body by first and second tubes, respectively, implanted within the body adjacent to the tumor.

9. The method of claim 8 further comprising removing gas that flows across the tumor from the body at the same rate as the gas is injected into the body.

10. The method of claim 9, wherein said removing comprises applying a vacuum to the second tube.

11. The method of claim 10 further comprising controlling the temperature and flow rate of the gas to provide a temperature of the order of 102° F. and a flow rate of the order of 2.4 CFM.

12. The method of claim 5, wherein the flowing fluid comprises a liquid flowing through a tube implanted within the body at the region of the tumor.

13. The method of claim 12, wherein the tube is implanted within the body in contact with the tumor.

14. The method of claim 12 further comprising controlling the temperature and flow rate of the liquid to provide a temperature of the order of 102° F. and a flow rate of the order of 15 ounces per second.

15. The method of claim 5 further comprising applying energy to the tumor for a period of time that is proportional to the size of the tumor.

16. A method of treating a tumor in a living body comprising implanting a tube within the body adjacent to the tumor, passing a flowing fluid into the body through the tube, the fluid having a temperature within the normal operating temperature range of the body, removing the flowing fluid from the body, and adjusting the flow rate of the fluid to a value that is effective to substantially destroy tumor cells without substantially destroying healthy cells.

17. The method of claim 16, wherein the fluid comprises a gas injected into the body adjacent to the tumor such that a gas flow across the tumor is produced, and wherein the gas flowing across the tumor is removed by another tube implanted within the body.

18. The method of claim 16, wherein the fluid comprises a liquid that flows into and out of the body via the tube.

19. The method of claim 16 further comprising subjecting the tumor to said flowing fluid for a period of time that is proportional to the size of the tumor.

20. The method of claim 16, wherein the temperature of the fluid is in the range of about 96° F. to 102° F.

* * * * *